United States Patent [19]

Beckerbauer et al.

[11] Patent Number: 5,206,440
[45] Date of Patent: Apr. 27, 1993

[54] OXIDATION OF FLUORINE CONTAINING SULFIDES TO SULFONES

[75] Inventors: Richard Beckerbauer, Wilmington, Del.; Shlomo Rozen, Tel Aviv, Israel

[73] Assignee: E. I. Du Pont de Nemours and Company, Wilmington, Del.

[21] Appl. No.: 920,514

[22] Filed: Jul. 28, 1992

Related U.S. Application Data

[63] Continuation of Ser. No. 822,790, Jan. 21, 1992, abandoned.

[51] Int. Cl.$^5$ ................ C07C 315/02; C07C 209/68; C07C 255/02; C07C 381/00
[52] U.S. Cl. ................................. 568/35; 568/32; 568/31; 568/30; 568/34; 558/437; 564/488; 564/500; 564/453; 560/150; 560/125
[58] Field of Search .............. 568/35, 30, 31, 32, 568/34; 558/437; 564/488, 500, 453; 560/150, 125

[56] References Cited

U.S. PATENT DOCUMENTS 5,084,583  1/1992  Rozen et al. ................ 549/523

OTHER PUBLICATIONS

Shlomo Rozen et al., "Epoxidation of Olefins with Elemental Fluorine in Water/Acetonitrile Mixtures", Angew. Chem. Int. Ed. Engl. 25 (1986) No. 6.
Shlomo Rozen et al., "Olefin Epoxidation Using Elemental Fluorine", Am. Chem. Soc., Feb. 7, 1990 (J. Org. Chem., vol. 55, No. 17 (1990).
Moshe Kol et al., "Oxidizing Aromatic Amines to Nitroarenes with the HOF-MeCN System", J. Chem. Soc., Chem. Commun., 1991, pp. 567–568.
Kondratenko et al. "Electronic Nature of Perfluoroalkylthioperfluoro-alkylseleno- and Perfluoroalkylthelluro-containing substitutents", J. Org. Chem., USSR (16) pp. 1049–1054, 1980.
Hsiung et al., "Langmuir-Blodgett Films of Fluorinated Polymers for Nonlinear Optics", Abstract published as part of proceedings 5th Intl. Conf. on L-B Films, Paris (Aug. 26–30, 1991) pp. 1–2.
Rozen et al., Journal of Organic Chemistry, vol. 55, pp. 5155–5159, 1990.

*Primary Examiner*—Marianne M. Cintins
*Assistant Examiner*—Margaret J. Page
*Attorney, Agent, or Firm*—Susan B. Evans

[57] ABSTRACT

A process for production of fluorinated sulfones from fluorinated organic sulfides by oxidation of the sulfides with an oxidizing reagent made from fluorine, water and acetonitrile. The sulfones are useful as second order nonlinear optical dyes.

13 Claims, No Drawings

OXIDATION OF FLUORINE CONTAINING SULFIDES TO SULFONES

This is a continuation, of application Ser. No. 07/822,790 filed Jan. 21, 1992, now abandoned.

FIELD OF THE INVENTION

This invention relates to the production of sulfones from fluorine containing sulfides, using elemental fluorine in mixtures of water and acetonitirile.

BACKGROUND OF THE INVENTION

1. Field of the Invention

The direct oxidation of organic sulfides to sulfones is a well known process, using common oxidizing agents such as peracids. However, when fluorine atoms are present close to the sulfide sulfur atom, and particularly if the fluorinated group is sterically hindered, the oxidation becomes more difficult. Such sulfides were reported by N. V. Kondratenko, et al., J. Org. Chem. USSR (translation), vol. 16, p. 1049-1054 (1980), to be oxidized to sulfones in moderately good yields by chromic anhydride or concentrated $H_2O_2$/trifluoroacetic acid/trifluoroacetic anhydride, both powerful oxidizing agents.

2. Technical Background

The instant invention, oxidation of fluorinated sulfides to sulfones using a combination of fluorine/water/aceto-nitrile as the oxidizing agent, yields the desired sulfones under mild conditions and in good yields.

The combination of fluorine/water/acetonitrile has been reported to epoxidize fluorinated olefins (U.S. Pat. No. 5,084,583), and to oxidize aromatic amines to nitroarenes, (M. Kol and S. Rozen, J. Chem. Soc., Chem. Commun., p. 567-568, 1991). No mention is made in either paper of oxidation of sulfides to sulfones.

SUMMARY OF THE INVENTION

This invention concerns a process for oxidizing sulfides to sulfones, comprising, contacting an oxidizing agent made from fluorne, water and acetonitrile with a sulfide of the formula $R^1SR^2$ wherein $R^1$ is hydrocarbyl or substituted hydrocarbyl, both not containing olefinic or acetylenic bonds; $R^2$ is perfluoroalkenyl or $—CR^3R^4R^5$; $R^3$ and $R^4$ are each independently fluorine, perfluoroalkyl, perfluoroalkenyl, or hydrocarbyl or substituted hydrocarbyl not containing olefinic or acetylenic bonds; $R^5$ is fluorine, perfluoroalkyl, perfluoroalkenyl, hydrocarbyl or substituted hydrocarbyl not containing olefinic or acetylenic bonds, or hydrogen; and provided that at least two of $R^3$, $R^4$ and $R^5$ are fluorine, perfluoroalkenyl, or perfluoroalkyl.

DETAILED DESCRIPTION OF THE INVENTION

When diluted fluorine is passed through a cold mixture of acetonitrile and water, an oxidizing reagent, stable at temperatures of up to 25° C. for several hours, is formed. Unlike many other oxidizing reagents, this oxidizing reagent can be used to oxidize fluorinated sulfides to sulfones in a convenient way, and with high yields of sulfone. It has been reported (S. Rozen and M. Kol, J. Org. Chem., vol. 55, p. 5155-5159, 1990) that in mixtures of fluorine/acetonitrile/water the "true" oxidizing agent is $HOF \cdot CH_3CN$.

Fluorine is of course a strong oxidizer and a very corrosive material. An appropriate vacuum line made from copper or monel should be constructed in a well ventilated area for working with this element. The oxidation of the sulfides can be carried out in glass vessels.

Mixtures of up to about 25%, preferably about 10-15% fluorine diluted with an inert gas such as nitrogen are used in the preparation of the oxidizing reagent. The gas mixtures are typically prepared in a secondary container before passing into the water/acetonitrile mixture. The gas is then passed (a typical rate is 400 ml/min) through a cold and vigorously stirred mixture of acetonitrile and water. The ratio of acetonitrile to water is about 10:1 by volume. The formation of the oxidizing reagent can be monitored by reacting aliquots with an acidic aqueous solution of potassium iodide, and then titrating the liberated iodine with thiosulfate. Concentrations of more than one mole/L of oxidizing reagent can be obtained.

The sulfones are produced according to the reaction:

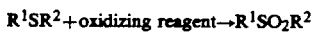

$$R^1SR^2 + \text{oxidizing reagent} \rightarrow R^1SO_2R^2$$

The sulfones produced by this reaction are useful in second order nonlinear optics, see for example R. Beckerbauer, et al., Abstracts of "Supramolecular Aspects of Polymer Synthesis and Polymer Structure" held Sep.30-Oct. 2, 1991, Max-Planck-Institut fur Polymerforschung, Mainz, Germany; H. Hsiung, et al., Proceedings of the 5th International Conference on Langmuir-Blodgett Films, Paris, Aug. 26-30, 1991; and published PCT application WO 9108198.

Theoretically, in order to convert one mole of sulfide to sulfone, two equivalents of oxidizing reagent are needed. It is preferred to use an excess of oxidizing reagent, and about 3 equivalents of oxidizing reagent per mole of sulfide is more preferred.

Fluorinated sulfides suitable for use in the oxidation of the present invention are those of the formula $R^1SR^2$ wherein $R^1$ is hydrocarbyl or substituted hydrocarbyl, both not containing olefinic or acetylenic bonds; $R^2$ is perfluoroalkenyl or $—CR^3R^4R^5$; $R^3$ and $R^4$ are each independently fluorine, perfluoroalkyl, perfluoroalkenyl, or hydrocarbyl or substituted hydrocarbyl not containing olefinic or acetylenic bonds; $R^5$ is fluorine, perfluoroalkyl, perfluoroalkenyl, hydrocarbyl or substituted hydrocarbyl not containing olefinic or acetylenic bonds, or hydrogen; and provided that at least two of $R^3$, $R^4$ and $R^5$ are fluorine, perfluoroalkenyl, or perfluoroalkyl. By hydrocarbyl is meant a univalent group containing only carbon and hydrogen. "Olefinic" and "acetylenic" are here given their common meaning of carbon-carbon double and triple bonds respectively, and do not include bonds in aromatic rings.

By substituted hydrocarbyl is meant hydrocarbyl groups containing substituents that do not interfere with, or are substantially affected by, the oxidizing reaction or oxidizing reagent. This generally means substituents that are not readily oxidized. Suitable substituents include, but are not limited to, fluorine, chlorine, ether (between hydrocarbyl segments), amide, nitro, cyano, oxo (ketone group) and ester.

In preferred sulfides, $R^1$ is alkyl, phenyl and p-fluorophenyl. In other preferred sulfides $R^2$ is perfluoroalkenyl or $—CR^3R^4R^5$ wherein $R^3$ and $R^4$ are fluorine and $R^5$ is perfluoroalkyl, particularly perfluoro-n-alkyl; and $R^3$, $R^4$ and $R^5$ are perfluoroalkyl, particularly perfluoro-n-alkyl. In more preferred sulfides, $R^2$ is perfluoro-n-hexyl, perfluoro-t-butyl, perfluoro(1,1- dimethyl-n-butyl), and perfluoro(1-methyl-2,2-diisopropylvinyl).

The fluorinated sulfides used herein can be made by known methods, see for example N. V. Kondratenko, et al., supra and references therein. Also see references cited in the Examples herein.

A suitable temperature range for the process of the present invention is from about −15° C. to about 30° C., preferably about 0° C. to about 25° C. Reaction times can range from about 1 minute to 3 hours or more. A typical reaction time is 2 to 3 hours.

Although not essential, the sulfide is usually dissolved in a solvent before mixing with the oxidizing reagent. Suitable solvents include methylene chloride, chloroform, acetonitirile, and fluorocarbons.

The following General Procedures are illustrative of typical preparation methods.

General Procedure for Producing the Oxidizing Reagent

Mixtures of 10–15% $F_2$ in $N_2$, prepared in a secondary container, are passed at a rate of about 400 ml/min through a vigorously stirred solution of 400 ml of $CH_3CN$ and 40 ml of water cooled to −10° C. The formation of the oxidizing power is monitored by reacting aliquots with an aqueous, acidic solution of KI; the liberated iodine is then titrated with thiosulfate. Concentrations of more than 1 mole/liter oxidizing reagent can be prepared.

General Oxidation Procedure

An appropriate amount of sulfide, dissolved in 30–50 ml of methylene chloride (ca. 0.02–0.04 g/ml), cooled to 0° C., is added in one portion to the reaction vessel in which the oxidizing reagent had been prepared. At least a 3 fold molar ratio of oxidizing agent/sulfide is used (2 mole/eq are needed to provide 2 oxygen donors). The cooling bath is then removed and, after 1–2 hours, the reaction is stopped by the addition of saturated sodium bicarbonate solution. (The reaction can be left much longer but this does not have any effect since most of the reagent is decomposed after 2–3 hours.) The reaction mixture is poured into water (about 3 times the volume of the reaction mixture), extracted with methylene chloride which is then washed with dilute sodium bicarbonate solution and water until neutral to pH paper. The organic layer is dried over $MgSO_4$ and stripped of solvent on a rotary evaporator. The crude product is either distilled under reduced pressure or, when solid, purified by flash chromotography and/or recrystallization.

EXAMPLE 1

Oxidation of p-fluorophenylperfluoro-n-hexylsulfide (1) to p-fluorophenylperfluoro-n-hexylsulfone (2)

A solution of 0.9 g (2 mmole) of the sulfide (1) in 30 ml of methylene chloride was added to 230 mmoles of oxidizing solution. After 1 hour at room temperature the reaction was worked up as described above. The sulfone was formed in quantitative yield as determined by VPC. The product, after removal of solvent, was a pale yellow oil (b.p.*=260.5° C., n=1.3930) which crystallized on cooling to a white solid (m.p.=22°–25° C.). The IR spectrum has new peaks (absent in starting sulfide) at 810, 1380, 1410 and 3115 $cm^{-1}$; $^1H$ NMR=7.19 ppm (2H, m), 8.09 (2H, m); $^{19}F$ NMR=−81.2 ppm (3F, t. J=10 Hz), −97.8 (1F arom, heptet. J=4 Hz), −111.6 (2F, t, J=14 Hz)−120, −122, −123 (each 2F, broad signals), −126.5 (2F, m); MS m/e=459 (M−F)+, 159($FC_6H_4SO_2$)+, 95($FC_6H_4$)+ and 69 ($CF_3$)+. *Boiling point by ultramicro method, uncorrected ("Microscale Organic Laboratory", D. W. Mayo, R. M. Pike and S. S. Butcher, p. 59, John Wiley & Sons, New York, 1986).

EXAMPLE 2

Oxidation of p-fluorophenyl nonafluorotert-betylsulfide (3) to p-fluorophenyl nonafluorotert-butylsulfone (4)

A cold solution of 1.4 g of the sulfide (3) in 30 ml of methylene chloride was added to 297 mmoles of the oxidizing solution. After 1 hr at room temperature the reaction was worked up as above. The sulfone (4) was formed in 94% yield, m.p.=56° C. (recrystallized from methanol) (lit. m.p.=59° C., from pentane, N. V. Kondratenko, et al., supra.). IR spectrum has major peaks at 780, 1380, 1415 and 3120 $cm^{-1}$ which are absent in the starting sulfide. $^1H$ NMR=7.3 ppm (2H, m) and 8.1 (2H, m): $^{19}F$ NMR=−62.1 ppm (9F, s) −97.5 (1F, aromatic, heptet. J=4 Hz); MS m/e=378 (M)+, 159 ($FC_6H_4SO_2$)+, 95 ($FC_6H_4$)+ and 69($CF_3$)+.

EXAMPLE 3

Oxidation of p-fluorophenyl 2-tridecafluoro-2-methyl pentylsulfide (5) to p-fluorophenyl 2-tridecafluoro-2-methylpentylsulfone (6)

A cold solution of 9.44 g of the sulfide (5), prepared by the reaction of p-fluorophenylsulfenylchloride, KF and dodecafluoro-2-methyl-2-pentene in DMF-b.p.=58° C./1.5 Torr, 1H NMR=7.1 ppm (2 H, m) and 7.7 (2H, m), 19F NMR=−61.5 ppm (6F, quint.), −80.78 (3F, t), −105.35 (2F, m), −107.15 (1F, aromatic, m J=4 Hz) and −122.5 (2F, m) following D. N. Harpp, F. T. Friedlander and R. A. Smith, Synthesis, Communications p. 181 (1979), in 50 ml of methylene chloride was added to 400 mmoles of the oxidizing solution. After standing for 1 hr at room temperature the reaction was worked up as described above. The sulfone (6) was formed in 74% yield, m.p.=44° C. (recrystallized from methanol). IR spectrum has major peaks at 780, 1385, 1420 and 3120 $cm^{-1}$; $^1H$-NMR=7.3 ppm (2H, m) and 8.1 (2H, m); $^{19}F$-NMR=−59.3 ppm (6F, heptet, J=9 Hz), −80.6 (3F, t. J=14 Hz), −97.7 (1F, aromatic, heptet. J=5 Hz), −103.0, −121.3 (each 2F, m); MS m/s=459 (M−F)+, 159 ($FC_6H_4SO_2$)+, 95 ($FC_6H_4$)+ and 69 ($CF_3$)+.

EXAMPLE 4

Oxidation of p-fluorophenyl 2-heptafluoro-3-iso-propyl-4-methylpentenylsulfide (7) to p-fluorophenyl 2-heptafluoro-3-iso-propy-4-methylpentenylsulfone (8a) and the pent-3-enylsulfide isomer (8b)

A cold solution of 1.85 g of a mixture containing 80% of the sulfide (7), prepared by the reaction of p-fluorothiophenoxide and hexafluoropropene trimer mixture (K. N. Makarov, E. E. Nikolaeva and V. V. Snegirev, J. of Fluorine Chem. 48, 133 (1990)) in 30 ml of methylene chloride was added to 220 mmoles of cold oxidizing solution. After warming to room temperature for 1 hour the mixture was worked up as above. Analysis by VPC and VPC-MS showed a greater than 90% conversion to the sulfone (8). Washing with hexane and recrystallization from acetonitrile to remove small amounts of the more soluble sulfoxides and flash chromatography on alumina with elution by 25/1 hexane/ether gave in >98% purity a yellow solid, a mixture of two sulfone isomers - the one derived from the starting sulfide (8a) and a rearranged product, p-fluorophenyl heptafluoro-3-isopropyl-4-methyl-2-pent-3-enylsulfide (8b). $^1$H-NMR for 8a=7.92 ppm (2H, m) and 7.32 (2H, m); for 8b =8.03 ppm (2H, m) and 7.32 (2H, m); $^{19}$F-NMR for 8a= −53.7 ppm (3F, d. J=54 Hz), −68.2 (6F, s); −70.1 (6F,s), −97.5 (1F, aromatic, m. J=5 Hz), −149.8 (1F, m) and −156.7 (1F, m); for 8b = −54.7 ppm (3F, m), −69.9, −70.5 (12F, m), −146.9 (1F, s) and −152.8 (1F, m); MS m/e=571 (M−F)+, 159 (FC$_6$H$_4$SO$_2$)+, 95 (FC$_6$H$_4$)+ and 69(CF$_3$)+ for the mixture of isomers which is not well separated by VPC.

Although preferred embodiments of the invention have been described hereinabove, it is to be understood that there is no intention to limit the invention to the precise constructions herein disclosed, and it is to be further understood that the right is reserved to all changes coming within the scope of the invention as defined by the appended claims.

What is claimed is:

1. A process for oxidizing sulfides to sulfones, comprising, contacting an oxidizing agent made by passing fluorine through a mixture of water and acetonitrile with a sulfide of the formula R$^1$SR$^2$ wherein:
   R$^1$ is hydrocarbyl or substituted hydrocarbyl, both not containing olefinic or acetylenic bonds;
   R$^2$ is perfluoroalkenyl or —CR$^3$R$^4$R$^5$;
   R$^3$ and R$^4$ are each independently fluorine, perfluoroalkyl, perfluoroalkenyl, or hydrocarbyl or substituted hydrocarbyl not containing olefinic or acetylenic bonds;
   R$^5$ is fluorine, perfluoroalkyl, perfluoroalkenyl, hydrocarbyl or substituted hydrocarbyl not containing olefinic or acetylenic bonds, or hydrogen; and provided that at least two of R$^3$, R$^4$ and R$^5$ are fluorine, perfluoroalkenyl, or perfluoroalkyl.

2. The process as recited in claim 1 wherein at least two equivalents of said oxidizing reagent are used per mole of said sulfide.

3. The process as recited in claim 2 wherein about three equivalents of said oxidizing reagent are used per mole of said sulfide.

4. The process as recited in claim 1 carried out at a temperature of about −15° C. to about 30° C.

5. The process as recited in claim 4 wherein said temperature is about 0° C. to about 25° C.

6. The process as recited in claim 1 wherein said R$^1$ is alkyl, phenyl or p-fluorophenyl.

7. The process as recited in claim 1 wherein said R$^2$ is perfluoroalkenyl or —CR$^3$R$^4$R$^5$, wherein R$^3$ and R$^4$ are fluorine, and R$^5$ is perfluoroalkyl; or R$^3$, R$^4$ and R$^5$ are perfluoroalkyl.

8. The process as recited in claim 7 wherein said R$^2$ is —CR$^3$R$^4$R$^5$, wherein R$^3$ and R$^4$ are fluorine and R$^5$ is perfluoro-n-alkyl; or R$^3$, R$^4$ and R$^5$ are perfluoro-n-alkyl.

9. The process as recited in claim 7 wherein said R$^1$ is alkyl, phenyl or p-fluorophenyl.

10. The process as recited in claim 1 wherein said R$^2$ is perfluoro-n-hexyl, perfluoro-t-butyl, perfluoro-(1,1-dimethyl-n-butyl), or perfluoro(1-methyl-2,2-diisopropylvinyl).

11. The process as recited in claim 6 wherein said R2 is perfluoro-n-hexyl, perfluoro-t-butyl, perfluoro(1,1-dimethyl-n-butyl), or perfluoro(1-methyl-2,2-diisopropylvinyl).

12. The process as recited in claim 1 wherein said substituted hydrocarbyl is substituted with fluorine, chlorine, ether, amide, nitro, cyano, oxo, or ester substituents.

13. The process as recited in claim 1 wherein said substituted hydrocarbyl is substituted with fluorine or ether substituents.

* * * * *